(12) United States Patent
Mast et al.

(10) Patent No.: US 7,252,984 B2
(45) Date of Patent: Aug. 7, 2007

(54) ATTENUATED MUTANT NEWCASTLE DISEASE VIRUS STRAINS FOR IN OVO VACCINATION, METHOD FOR PREPARING AND THEIR USE

(75) Inventors: Jan Mast, Boutersem (BE); Guy Meulemans, Brussels (BE)

(73) Assignee: Centrum Voor Onderzoek in Diergeneeskunde en Agrochemie, Brussels (BE)

( * ) Notice: Subject to any disclaimer, the term of this patent is extended or adjusted under 35 U.S.C. 154(b) by 76 days.

(21) Appl. No.: 10/491,375

(22) PCT Filed: Oct. 2, 2002

(86) PCT No.: PCT/EP02/11081

§ 371 (c)(1),
(2), (4) Date: Mar. 31, 2004

(87) PCT Pub. No.: WO03/030932

PCT Pub. Date: Apr. 17, 2003

(65) Prior Publication Data

US 2004/0258713 A1 Dec. 23, 2004

(30) Foreign Application Priority Data

Oct. 4, 2001 (EP) .................... 01870211

(51) Int. Cl.
*C12N 7/04* (2006.01)
*C12N 7/02* (2006.01)
*C12N 7/00* (2006.01)

(52) U.S. Cl. .................... 435/236; 435/239; 435/235.1; 435/243

(58) Field of Classification Search ............. 435/235.1
See application file for complete search history.

(56) References Cited

FOREIGN PATENT DOCUMENTS

| EP | 0 583 998 A1 | 2/1994 |
| EP | 0 848 956 A1 | 6/1998 |
| EP | 0 974 660 A1 | 1/2000 |
| EP | 1 074 614 A1 | 2/2001 |
| WO | WO 99/66045 | 12/1999 |
| WO | WO 00/61737 | 10/2000 |

OTHER PUBLICATIONS

Seal et al. "Characterization of Newcastle disease virus vaccines by biological properties and sequence analysis of the hemagglutinin-neuraminidase protein gene" Vaccine vol. 14(1996), No. 8, pp. 761-766.*
Meulemans, G et al., entitled "Pathogenicity of Antigenic Variants of NewCastle Disease Virus Italian Strain Selected with Monoclonal Antibodies," Ann Rech Vet 1987 18: 371-374.
Alexander, D. J., entitled "Newcastle disease and other avian paramyxoviruses," Rev. sci. tech. Off. int. Epiz., 2000, 19 (2), 443-462.

* cited by examiner

*Primary Examiner*—Bruce R. Campell
*Assistant Examiner*—Bo Peng
(74) *Attorney, Agent, or Firm*—Amster, Rothstein and Ebenstein LLP

(57) ABSTRACT

The present invention relates to new attenuated mutant New Castle's disease La SotaNewcastle disease virus strains suitable for in ovo vaccination of avian species comprising a mutation in the gene sequences encoding the HN and/or F glycoproteins of said virus. Furthermore, the invention relates to a vaccine composition comprising said attenuated mutant Newcastle's disease La Sota virus strain, and to the use thereof for the preparation of a vaccine for in ovo vaccination of avian species against Newcastle's disease.

8 Claims, 6 Drawing Sheets

Figure 1:
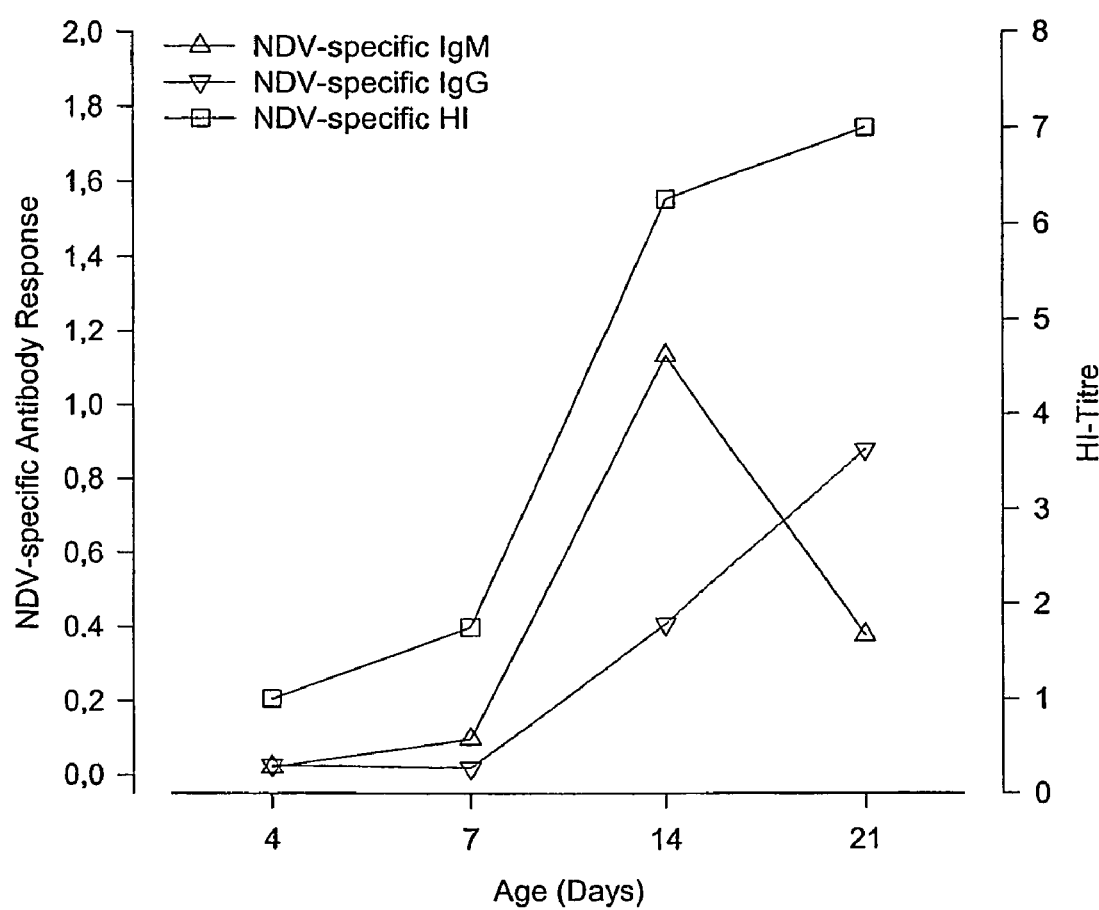

—○— $10^2$ EID$_{50}$ F+HN on ED18
—△— $10^3$ EID$_{50}$ F+HN on ED18
—▽— $10^4$ EID$_{50}$ F+HN on ED18
—◇— Control
—●— sentinel for $10^2$ EID$_{50}$ F+HN on ED18
—▲— sentinel for $10^3$ EID$_{50}$ F+HN on ED18
—▼— sentinel for $10^4$ EID$_{50}$ F+HN
—◆— sentinel for control

Figure 4

ATTENUATED MUTANT NEWCASTLE DISEASE VIRUS STRAINS FOR IN OVO VACCINATION, METHOD FOR PREPARING AND THEIR USE

This application is a national stage entry under 35 U.S.C. §371 of PCT International Application No. PCT/EP02/11081, filed Oct. 2, 2002, which claims priority of European Patent Application No. 01870211.8, filed Oct. 4, 2001, the contents of which are incorporated herein by reference in their entirety.

FIELD OF THE INVENTION

The present invention concerns new attenuated mutant Newcastle disease virus strains. The invention includes a more general method for selecting attenuated virus strains based on the use of virus specific antibodies, and particular antibodies specific for Newcastle disease La Sota virus. The invention also includes the use of said attenuated mutant Newcastle disease virus La Sota strains in a vaccine for in ovo vaccination of avian species, preferably chickens.

BACKGROUND

Antibodies are powerful tools for analyzing mutations in antigens (Pollock et al. 1987) and they have been successfully used for selecting antigenic variants, also known as escape mutants, of influenza virus (Gerhard and Webster 1978, Lubeck et al. 1980, Yewdel et al. 1986), rabies virus (Wiktor and Koprowski 1980) and measles virus (Birrer et al. 1981). NDV escape mutants were produced by Russel (1983), Abenes et al. (1986), Meulemans et al. (1987) and Yussof et al. (1989). Meulemans et al. (1987) showed that NDV escape mutants may be more, or less pathogenic than the parental virus strains (Meulemans et al. 1987).

The production of antibody resistant virus strains to deliberately attenuate the parental virus and make it suitable as in ovo vaccine was never suggested. Benejean et al. (EP0583998) attenuated the rabies virus by producing an escape mutant and used it as a vaccine. They never suggested or implied the use of this technique to produce escape mutants of avian viruses possibly useful for in ovo vaccination.

In ovo vaccination technology using approved vaccine is a safe, efficacious, and convenient method for vaccination of poultry (Ricks et al. 1999, U.S. Pat. No. 6,032,612, AO1K45/00C). In 1999, more than 80% of the U.S. broiler industry had converted to the in ovo vaccination process to control Marek's disease (Ricks et al. 1999).

Studies within the last few years have shown that only few live vaccines that are routinely administered to hatched chickens may also be injected into embryonated eggs during late stages of embryonation without a toxic effect. The turkey herpes virus (HVT, Sharma and Burmester, 1982), and infectious bursal disease virus (IBDV) strains of low virulence (Sharma, 1985) can be used as embryo vaccines to induce active protection against the homologous strains.

IBDV strains of moderate virulence such as 2512 (Sharma 1985), commercial infectious bronchitis virus (IBV) strains such as Massachusetts 41 (Wakenell and Sharma 1986) and Newcastle disease virus strains such as the B1 (Ahmad and Sharma, 1992, 1993) and the La Sota strain, cannot be employed for in ovo vaccination in their current form due to embryonic toxicity. Attenuation of the virus strains currently used for post hatch vaccination is thus required to obtain strains with reduced pathogenicity to the avian embryo.

Wakenell and Sharma (1986) reduced the pathogenicity to the embryo of the Massachusetts 41 IBV strain using a tissue culture attenuation system. At the $40^{th}$ passage in chicken kidney tissue culture, the virus became apathogenic for the embryos and embryonic vaccination induced IBV specific antibody production and protection against virulent Massachusetts 41 IBV at 4 weeks of age.

Treatment of the B1 strain of NDV with the alkylating agent ethylmethane sulfonate markedly reduced the virulence of this strain for the 18-day chick embryo, and in ovo vaccination with this strain resulted in NDV specific antibody production and protection against challenge with the Texas GB strain (Ahmad and Sharma 1992). Further, it was claimed (EP0848956 A1) that a vaccine preparation containing Newcastle disease viruses of the strain NDW was particularly suited for in ovo application.

Finally, Mebatsion and Schrier (EP1074614A1) produced a NDV La Sota mutant, which is suited as vaccine candidate for in ovo vaccination. The mutant expresses reduced levels of V protein and can safely be administered to chicken embryos before hatch. No antibody-based selection was used to obtain these strains.

The formation of a complex between a measured amount of antibody with IBDV neutralizing activity and a specific amount of IBDV neutralized the pathogenicity of the IBDV and made it useful as in ovo vaccine (U.S. Pat. No. 5,871,748, Whithfill et al. 1992, 1995, Haddad et al. 1997).

In order to reduce the economic losses due to Newcastle disease in the commercial poultry industry, chickens currently have to be vaccinated against the Newcastle disease virus. It may be advantageous to use embryo vaccination for said purpose, in particular since in ovo injection can be done using semiautomatic machines with multiple injection heads allowing individual vaccination.

However, many vaccines used conventionally for post-hatch vaccination of birds cannot be used for in ovo vaccination. It is therefore an aim of the present invention to provide attenuated Newcastle disease virus strains which can be effectively used as a vaccine in avian species, administrable post hatch or in ovo. Another aim of the present invention is to provide a general method for selecting attenuated avian virus strains, and in particular attenuated strains of Newcastle disease virus.

DESCRIPTION

According to a first aspect, the present invention relates to an attenuated mutant Newcastle disease La Sota virus strain suitable for in ovo vaccination of avian species comprising a mutation in the gene sequences encoding the HN and/or F glycoproteins of said virus resulting in an altered expression of said glycoproteins.

The term 'attenuated strain' relates to a strain which is less virulent than the parental strain.

La Sota is a lentogenic Newcastle disease virus strain. Several pathotypes of Newcastle disease virus have been identified, i.e. velogenic, mesogenic and lentogenic. Although these terms result from laboratory tests carried out both in vivo and in vitro, the terms are now generally used to describe viruses of high, moderate or low virulence for chickens. The neurotropic velogenic form of the disease is caused by highly pathogenic strains of Newcastle disease virus and is characterised by a sudden onset of severe respiratory signs followed by neurological signs. In most cases the infected animals do not survive. Viscerotropic velogenic Newcastle disease virus strains are also highly pathogenic and cause high mortality and severe lesions in the gastrointestinal tract. Mesogenic strains of Newcastle disease virus usually cause severe respiratory disease in fully susceptible birds, and in adult birds cause a marked drop in egg production. Lentogenic strains of Newcastle disease virus cause generally a mild disease which is characterised by respiratory signs, especially in young fully susceptible birds.

The attenuated mutant Newcastle disease La Sota virus strains of this invention are suitable for in ovo vaccination of any avian animal, whether domestic or wild, and particularly those which are commercially reared for meat or egg production. Without limitation thereto, exemplary avian species include chickens, turkeys, pigeons, pheasants, and the like. Birds, which are reared in high density brooder houses such as broiler and layer chickens, are especially vulnerable to environmental exposure to infectious agents and would largely benefit from pre hatch vaccination. Preferably, chickens, turkeys and pigeons are used.

As will be explained further below in this description and particularly in example 1, HN and F antigenic variant virus strains were obtained from the lentogenic La Sota Newcastle disease strain by a process called immunoselection, using the Mabs 8C11 (Le Long et al. 1986) and 1C3 (Le Long et al. 1988) directed against the F and the HN glycoproteins of Newcastle disease, respectively. Four strains were obtained in total. The F and HN strains were selected with monoclonal antibodies 1C3 and 8C11, respectively. In addition, two double mutants were produced by immunoselection using F and HN specific monoclonal antibodies 1C3 and 8C11 starting from the HN and F mutant strains, respectively.

These four attenuated Newcastle disease La Sota virus strains were further characterized in haemagglutination inhibition and ELISA tests and by sequence analysis of the genes coding for the F- and the HN-glycoproteins. These results are described in Table 3, 4 and 5 of example 2. Said characterization revealed that the different NDV-strains selected with the monoclonal antibody 1C3 are characterized by a substitution of amino acid 72 of the F gene. Indeed, the F-gene of the F and F+HN mutant strains selected using the monoclonal antibody 1C3 differ from the parental La Sota strain by a point mutation G-to-T (GAT to TAT) leading to an Asp-72-Tyr substitution. Immunoselection of the HN-mutant, characterized by a Arg-101-Met substitution in the F gene, with 1C3 to obtain the HN+F mutant resulted in an additional Asp-Glu substitution at this same amino acid 72. The Asp-72-Tyr substitution was observed earlier in a 1C3-resistant mutant of the Beaudette strain (Yusoff et al. 1989) while an Asp-72-Gly transition was observed in 1C3-resistant mutants of the Italien NDV strain (Neyt et al. 1989), the Beaudette C strain (Yusoff et al., 1989) and in an antigenic variant of the Sato strain (Toyoda et al. 1988). Determination of the three-dimensional structure of the fusion protein of NDV showed that the involved 1C3-epitope is surface exposed and situated at the loop segment between strand IIIa and the interchain disulfide (Chen et al. 2001) at antigenic sites A1, II and 1. Site A1 is as defined by Yusoff et al. (1989), II is as defined by Toyoda et al. (1988) and 1 is as defined by Neyt et al. (1989). Table 4 illustrates that the F–, F+HN– and HN+F mutants did not only lose the 1C3-epitope, but also the 10F2-epitope situated on the same loop (Chen et al. 2001), whereas a nearby, third epitope on this loop, defined by monoclonal antibody 2C1, was conserved. In none of the F-NDV mutant strains the point mutation Asp-72-Gly affects the recognition of the antigenic site A5, I, 2, defined by monoclontal antibody 12C4. Chen et al. (2001) showed based on their three-dimensional model of the F-protein that this epitope is determined by surface-exposed residues at a distant loop segment, between strands If and Ig.

Finally, an Arg-101-Met substitution was observed in the HN and the HN+F mutants, which did not result in an altered recognition by the tested monoclonal antibody in ELISA and neither did the mutations at amino acids 320 and 467 of the F-gene (Table 5), as they were conservative.

Immunoselection with the HN-protein specific monoclonal antibody 8C11 induced point mutations in the gene of this protein. Sequence analysis (Table 5) demonstrated Leu-193-Ser substitutions in the HN and HN+F strains, and a Leu-160-Gln substitution in the HN+F strain. Furthermore, a conservative ACA to ACG mutation is observed in codon 41 in both these strains. None of these mutations result in the loss of an epitope recognized by HN-protein-specific MAb, as assessed by ELISA (Table 4).

However, the haemagglutination induced by the HN+F mutant is not inhibited by the monoclonal antibody 8C11, which was used for selection, indicating that the 8C11 epitope, although expressed, might not be functionally active anymore. The haemagglutination mediated by the HN mutant is not inhibited, or reduced in comparison to the original La Sota strain, by several monoclonal antibodies. This possibly indicates defective expression and functioning of its entire HN molecule.

Sequence analysis further demonstrated that the F and the derived F+HN mutant are characterized by Asn-115-Ser and Arg-124-Gly substitutions in the HN-protein. These mutations do not influence the recognition of the F mutant by the examined monoclonal antibody in ELISA (Table 3) or the haemagglutination inhibition assay (Table 4). The lack of reactivity of the monoclonal antibody 8C11 with the F+HN mutant in these assays must therefore be entirely attributed to the observed Leu-229-Arg substitution. Likewise, this substitution appears to induce the recognition of this La Sota mutant strain by a Hichner strain specific monoclonal antibody 10B12 in the HI, but not in the ELISA assay.

According to an embodiment, the present invention relates to an attenuated mutant Newcastle disease La Sota virus strain as described above characterized in that its haemagglutination is not inhibited by monoclonal antibody 8C11 which specifically recognises Newcastle disease virus glycoprotein HN.

Haemagglutination inhibition assays are well known in the art and allow to investigate the expression of functionally active epitopes on said virus strains. As mentioned before, the characterization of the attenuated mutant Newcastle disease La Sota virus strains F, HN, HN+F and F+HN in such haemagglutination inhibition assays is described in example 2 and Tables 2 and 3. With no inhibition of haemagglutination is meant a signal less than 2.

According to another embodiment, the present invention also relates to an attenuated mutant Newcastle disease La Sota virus strain as defined above characterized in that it is not recognized by monoclonal antibody 8C11 in an indirect ELISA assay, wherein said monoclonal antibody 8C11 specifically recognizes Newcastle disease virus glycoprotein HN. No binding to said antibody indicates that the final signal (O.D. or absorbance) obtained in the ELISA assay is less than 0.120.

According to yet another embodiment, the present invention further relates to an attenuated mutant Newcastle disease La Sota virus strain as described above characterized in that it is not recognized by monoclonal antibodies 1C3 or 10F2 in an indirect ELISA assay, wherein said monoclonal antibodies specifically recognize Newcastle disease virus glycoprotein F.

Indirect ELISA assays are well known in the art and binding of the virus strains HN, F, HN+F and F+HN in such an assay is given in example 2 and Table 4.

According to yet another embodiment, the present invention also relates to an attenuated mutant Newcastle disease La Sota virus strain as described above and deposited as La Sota mutant 1C3+8C11, under registration number CNCM I-2714, in the National Collection of Cultures of Microorganisms of the Pasteur institute in Paris. Surprisingly, said attenuated mutant Newcastle disease La Sota virus strains have been found suitable for in ovo vaccination. This is further illustrated in example 3. The pathogenicity of both the HN and the F virus strain was reduced substantially in comparison with the parental lentogenic La Sota strain from which they were derived. Moreover, the pathogenicity of both the HN+F and the F+HN mutant strains was even more drastically reduced in comparison with the parental La Sota strain. Hatchability and neonatal survival were generally higher for chicks inoculated with the double mutant strains than with the F and HN strains.

In ovo vaccination involves the administration of said attenuated virus strains to eggs. Said eggs are fertile eggs which are preferably in the fourth quarter of incubation. Chicken eggs are treated on about the fifteenth to nineteenth day of incubation, and are most preferably treated on about the eighteenth day of incubation. Turkey eggs are preferably treated on about the twenty-first to twenty-sixth day of incubation, and are most preferably treated on about the twenty-fifth day of incubation.

Eggs may be administered the vaccine of the invention by any means which transports the compound through the shell. The preferred method of administration is, however, by injection. The site of injection is preferably within either the region defined by the amnion, including the amniotic fluid and the embryo itself, in the yolk sac, or in the air cell. Most preferably, injection is made into the region defined by the amnion. By the beginning of the fourth quarter of incubation, the amnion is sufficiently enlarged that penetration thereof is assured nearly all of the time when injection is made from the center of the large end of the egg along the longitudinal axis.

The mechanism of injection is not particularly critical provided that it does not unduly damage tissue and organs of the embryo. For example, a small hole is pierced with a needle (1-1½ inch, about 22 gauge) attached to syringe in the large end of the shell and the vaccine is injected below the inner shell membrane and the chorioallantoic membrane. Subsequently, the vaccinated embryonated eggs are transferred to an incubator to hatch. Several devices are available for said in ovo vaccination, exemplary being those disclosed in U.S. Pat. Nos. 4,681,063; 4,040,388; 4,469,047 and 4,593,646.

Although in ovo injection of the live virus strains according to the present invention is preferable, these viruses can also be administered by the mass application techniques commonly used for ND vaccination. These techniques include drinking water and spray vaccination. Because of the extremely mild properties of the vaccine, spray administration of the vaccine is in particular contemplated.

The attenuated Newcastle disease La Sota virus strains of the present invention may be incorporated in a vaccine. Therefore, the present invention also relates to a vaccine composition which provides protective immunity against Newcastle disease comprising an attenuated mutant Newcastle disease La Sota virus strain as mentioned above.

In example 4 results are described illustrating that administration of mutant viruses to SPF embryos induces a virus specific immune response.

The vaccine according to the invention may be prepared and marketed in the form of a suspension or in a lyophillised form and additionally contains a pharmaceutically acceptable carrier or diluent customary for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthuilate and gentamicin. Diluents include water, aqueous buffer (such as buffered saline) and polyols (such as glycerol).

The composition of the present invention may also be used for in ovo vaccination as a mixed vaccine in combination with at least one vaccine selected from the group consisting of vaccines to other viruses such as e.g. avian infectious bronchitis virus, avian infectious bursal disease virus, avian encephalomyelitis virus, egg drop syndrome virus, influenza virus, reovirus, adenovirus, etc.; bacteria such as e.g. *Haemophilus paragallinarum, Salmonella typhimurium, S. enteritidis, S. pullorum, S. gallinarum, E. coli, Clostridium* spp., *Campylobacter* spp., *Mycoplasma* spp., etc.; and protozoans such as e.g. *Eimeria tenella, E. maxima, E. acervulina, E. brunetti, E. necatrix*, chicken malaria, etc.

According to yet another aspect, the present invention relates to the use of an attenuated mutant Newcastle disease La Sota virus strain of the invention as described above for the preparation of a vaccine for in ovo vaccination of avian species against Newcastle disease.

According to another embodiment, the attenuated mutant Newcastle disease La Sota virus strain of the invention as described above may also be used for the preparation of a vaccine of avian species for post-hatch application According to yet another aspect, the present invention relates to a method for producing a vaccine for in ovo vaccination of avian species, said vaccine comprising attenuated mutant avian virus strains, which are selected using virus specific antibodies.

Thus, the invention relates to a method of producing virus strains with reduced embryonic pathogenicity using a selection method based on specific antibodies or fragments thereof. By culturing virus in the presence of antibodies, virus particles with an altered recognition by the practiced antibodies may be selected. By repeating this selection serially, antibody resistant virus strains may be obtained. The multiplication of the selected virus between selections may be required.

The system to culture the virus in the presence of antibodies is not critical. Virus culture systems may consist of entire, or parts of tissues, isolated avian or mammalian cells, or fertilized eggs. Cells may be primary cultures or established cell lines.

The antibodies used in practicing the present invention are virus specific antibodies. Virus specific antibodies are those, which interact with the virus if the virus and the antibodies are allowed to react together for a sufficient time. The source of the virus specific antibodies is not critical. They may originate from any animal including mammals (mouse, rat, rabbit) and birds (e.g. chicken, turkey).

The present method of the invention is particularly apparent in the prevention of lethal diseases, which threaten birds early in life. One of the most prevalent and economically destructive diseases of the poultry industry is Newcastle disease.

However, the method of selecting attenuated mutant virus strains using virus specific antibodies may also be extended to other immunizable avian viral diseases.

The virus strains obtained by said immunoselection may be multiplied in a tissue culture system, such as an in vitro culture of cells, or in an in vivo system, such as fertilized chicken eggs.

Subsequent screening by inoculation of avian embryos allows selecting those virus strains with reduced pathogenicity. If the produced virus strains induce an active immune response, which may be protective, they may be used as vaccine. Based on differences in immune responses induced by the antigenic variants, produced as described above, subjects vaccinated with these variants may be discriminated. An example for this is the discrimination of chicks vaccinated with mutant Newcastle disease La Sota strains from chicks vaccinated with the parental La Sota strain based upon differences in the virus specific antibodies.

The principle of the preparation of attenuated Newcastle disease virus strains by immunoselection is explained in full detail in example 1. In said example the selection is done using monoclonal antibodies 8C11 and 1C3 directed against HN and F glycoproteins, respectively.

According to another embodiment, the present invention also relates to the method as described above wherein said virus specific antibodies are specific for viral avian diseases selected from the group consisting of Newcastle disease, infectious bronchitis, infectious bursal disease, adenovirus diseases, reovirus, pox, laryngotracheitis and influenza.

Avian viruses causing said diseases are hereby included, such as avian herpesviruses (e.g. avian infectious laryngotracheitis, Marek's disease virus, . . . ), avian coronaviruses (e.g. avian infectious bronchitis virus, turkey enteritis virus, . . . ), avian birnaviruses (e.g. infectious bursal disease virus), avian enteroviruses (e.g. avian encephalomyelitis virus), avian astroviruses, avian adenoviruses group I, II and III, avian pneumoviruses (e.g. avian rhinotracheitis virus), avian reovirus (e.g. viral arthritis virus), avian circoviruses (e.g. chicken anemia virus) and avian poxviruses. In principle, the method can be applied to all avian viruses for which neutralizing monoclonals or polyclonal antiserum is available.

As mentioned above, in case of Newcastle disease, neutralizing antibodies which are directed against the For HN viral glycoprotein were used in the examples described further below in this description.

Therefore, according to another embodiment, the present invention also relates to the method as mentioned above wherein said virus specific antibodies specifically recognize an epitope on Newcastle disease virus glycoproteins HN and/or F.

Attenuated mutant Newcastle disease virus strains selected by said antibodies may be differentiated from the parental virus strain among others by their reactivity with MAb in ELISA and in haemagglutination assays or by the nucleotide sequence of their genes. The lack of neutralisation by homologous MAb after each passage in relation to the non-treated control virus may be used as criterion to distinguish antigenic variant or mutant virus from revertant virus (Fleming et al. 1986).

According to another embodiment, the present invention also relates to the method as mentioned above wherein said virus specific antibodies specifically recognize an epitope on Newcastle disease La Sota virus glycoprotein HN.

According to yet another embodiment, the present invention relates to the method as mentioned above wherein said virus specific antibodies specifically recognize an epitope on Newcastle disease La Sota virus glycoprotein F.

According to yet another embodiment, said virus specific antibodies as mentioned above are monoclonal antibodies 8C11 or 1C3.

According to yet another aspect, the present invention also relates to a vaccine obtainable by the method according to the invention suitable for in ovo vaccination of avian species against viral diseases.

According to another aspect, the present invention relates to a vaccine obtainable by the method according to the invention suitable for post-hatch vaccination of avian species.

According to yet another aspect, the present invention relates to the use of antibodies specifically recognizing an epitope of HN and/or F glycoproteins or proteins similar thereto on lentogenous virus strains for selecting an attenuated mutant virus strain.

According to another embodiment, the invention relates to the use of antibodies as mentioned above specifically recognizing an epitope of HN and/or F glycoproteins on Newcastle disease virus for selecting an attenuated mutant Newcastle disease virus strain.

According to yet another embodiment, the invention relates to the use of antibodies as mentioned above specifically recognizing an epitope on the HN or F glycoprotein of Newcastle disease La Sota virus for selecting an attenuated mutant La Sota virus strain.

According to yet another embodiment, the present invention relates to the use as mentioned above comprising the use of monoclonal antibodies 8C11 and/or 1C3.

The following examples are intended only to further illustrate the invention and are not intended to limit the scope of the invention, which is defined by the claims.

BRIEF DESCRIPTION OF THE FIGURES AND TABLES

Table 1. Neutralisation of antigenic variants after neutralisation using homologous MAb.

Table 2. Characterisation of NDV La Sota strains by haemagglutination inhibition assay using NDV specific MAb.

Table 3. Characterisation of NDV La Sota strains by haemagglutination inhibition assay using NDV specific MAb.

Table 4. Reactivities of NDV-specific MAb with different NDV strains in indirect ELISA.

Table 5. Sequence analysis of the genes coding for the F- and HN-glycoproteins of NDV La Sota strains Table 6. Influence of inoculation at ED18 with different doses of the NDV La Sota strain on the hatchability of SPF eggs.

Table 7. Influence of inoculation at ED18 with different doses of the NDV La Sota HN strain (Exp. 1-3) and the F mutant strain (Exp. 4) on the hatchability and neonatal survival.

Table 8. Influence of inoculation at ED18 with different doses of the NDV La Sota 1C3+8C11 (F+HN) strain on the hatchability and neonatal survival.

Table 9. Influence of inoculation at ED18 with different doses of the NDV La Sota double mutant strains on the hatchability of NDV negative eggs.

Table 10. Influence of inoculation at ED18 with different doses of the NDV La Sota HN+F strain on the hatchability of SPF eggs.

Table 11. Influence of inoculation at ED18 with different doses of the NDV La Sota double mutant F+HN on the hatchability of eggs and post hatch mortality of commercial broiler chickens.

Table 12. In ovo vaccination with indicated doses of the F+HN mutant strain and effect on survival of commercial broiler chickens after intramuscular challenge with $10^5$ $EID_{50}$ of the Texas GB strain on day 43 post hatch.

Figure 2:
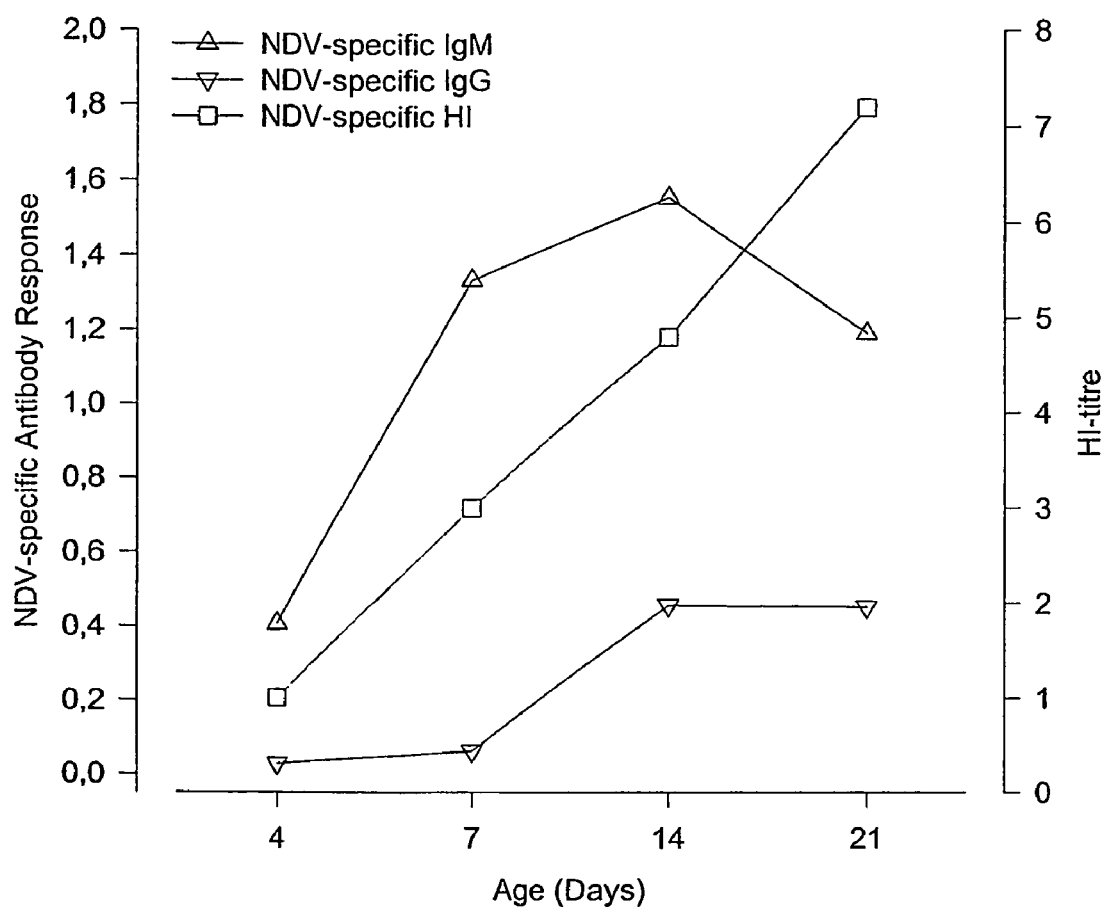

FIG. 1 Mean NDV specific responses of SPF chickens (n=4) upon in ovo vaccination with 100 EID50 of the La Sota HN mutant in function of age FIG. 2 Mean NDV specific responses of SPF chickens upon in ovo vaccination with 105 EID50 of the La Sota F+HN mutant in function of age. For 4 and 17 day old chicks, n=4, for 14 and 21 day old chicks, n=3.

Figure 3:
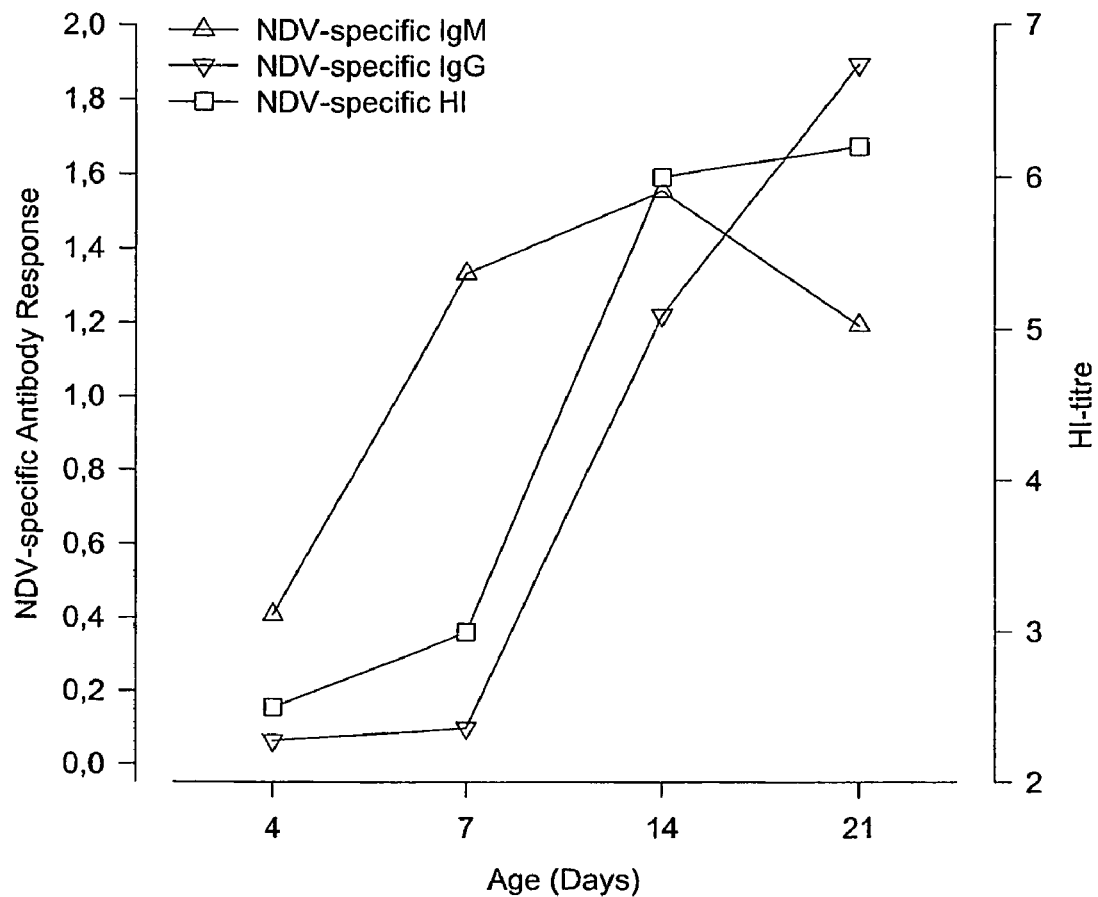

FIG. 3 Mean NDV specific responses of SPF chickens upon in ovo vaccination with 102 EID50 of the La Sota F+HN mutant in function of age. For 4 and 7 day old chicks, n=4, for 14 and 21 day old chicks, n=3.

FIG. 4 Mean NDV specific haemagglutination inhibition responses upon in ovo vaccination with the La Sota F+HN mutant in function of age. Open symbols represent commercial broiler chickens, closed symbols represent unvaccinated SPF chickens housed in the same isolator. The responses of the latter are a measure for dissemination of the vaccine virus.

Figure 5:
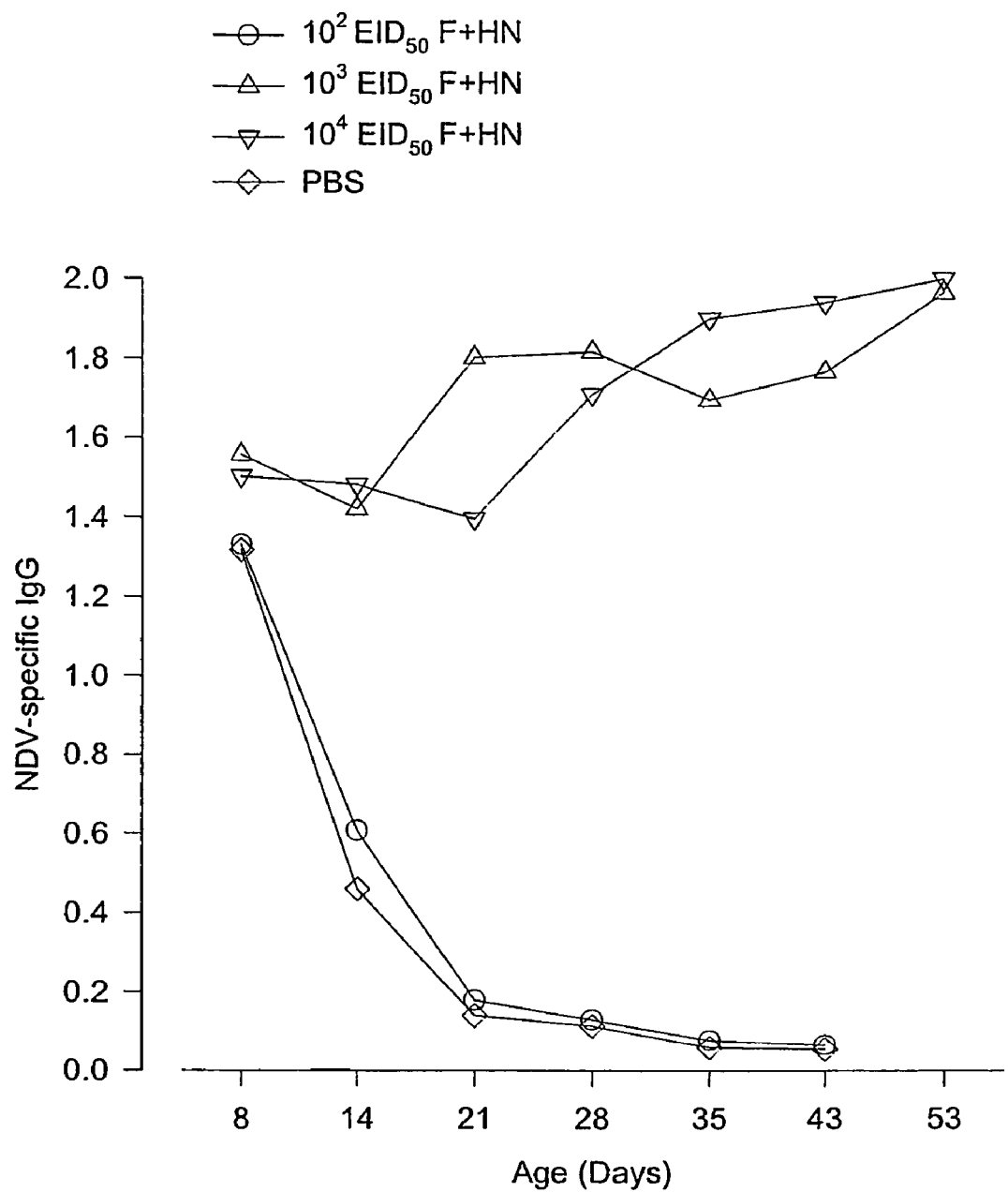

FIG. 5 Mean NDV specific IgG responses of commercial broiler chickens upon in ovo vaccination with the La Sota F+HN mutant in function of age.

Figure 6:
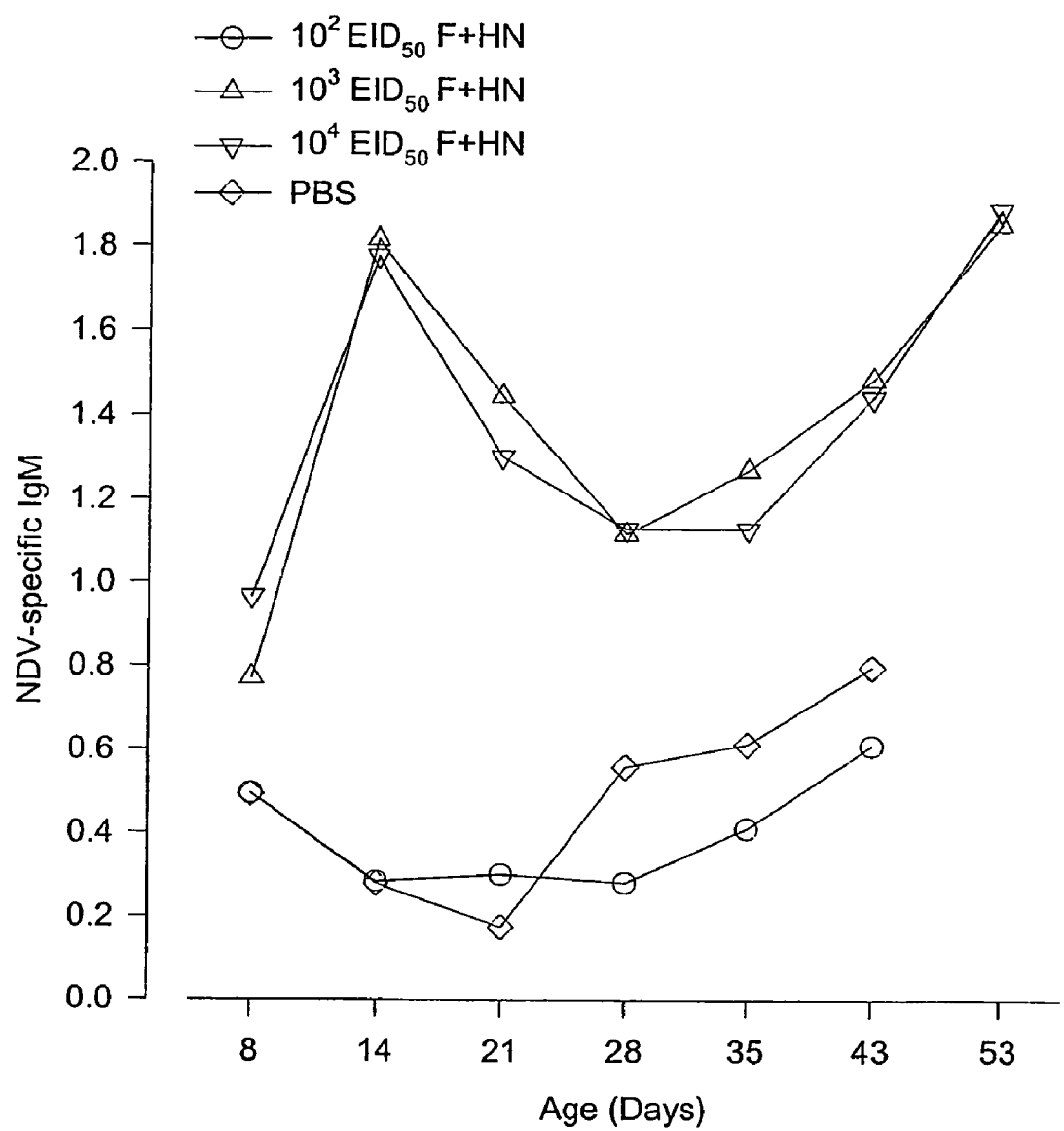

FIG. 6 Mean NDV specific IgM responses of commercial broiler chickens upon in ovo vaccination with the La Sota F+HN mutant in function of age.

EXAMPLES

Example 1

Preparation of Antibody Resistant NDV La Sota Strains by Immunoselection

HN and F antigenic variant viruses were obtained from the lentogenic La Sota NDV strain by immunoselection, as described by Meulemans et al. (1987), using the MAb 8C11 and 1C3 directed against these two viral glycoproteins, respectively.

After culture on embryonic chicken hepatocytes in the presence of one of these MAb, the antibody resistant virus was multiplied on 9 to 11 day old chicken SPF embryos. This procedure was repeated four times, successively. After each passage, the neutralisation by homologous MAb was examined and related to the non-treated control virus. Table 1 shows that after 4 passages, the HN- and F-mutant strains show strong resistance to neutralisation. For these antigenic variants, the virus titre after neutralisation using the homologous antibodies nearly differed with less than 1 log 10 from the untreated controles. The latter criterion was defined by Fleming et al. (1986) as criterion to distinguish antigenic variant from revertant virus.

In addition so called double mutants were produced by immunoselection as described above, using F and HN specific MAb 1C3 and 8C11 starting from the HN and F mutant strains, respectively. These strain were referred to as F+HN mutant, for the double mutant strain selected from the F mutant strain with the HN specific MAb 8C11, and HN+F mutant for the double mutant strain selected from the HN mutant strain with the F specific MAb 1C3. Table 1 indicates that these mutants can be regarded as true variant viruses on the basis of neutralisation results, according to the criterion of Fleming (1986), because for each of these antigenic variants the virus titre after neutralisation using the homologous MAb differed with less than 1 log 10 from the untreated control.

From Table 1, the frequency of an antibody resistant mutant in the parental virus population can be estimated as the ratio of the TCID50/ml of the virus in the presence of MAb after the first passage and the corresponding TCID50/ml of the virus without MAb. The approximate frequencies of 1C3 resistant mutants in the parental La Sota strain and the HN mutant strain are thus $10^{-5}$ and $10^{-6}$, respectively. The approximate frequencies of 8C11 resistant mutants in the parental La Sota strain and the HN mutant strain are $10^{-3}$ and $10^{-4}$, respectively. The frequency of finding the double mutants in the parental La Sota strain would thus be $10^{-9}$ for both the F+HN and the HN+F mutant.

Example 2

Characterization of NDV La Sota Mutant Strains

The produced La Sota strains were characterized based on the inhibition of haemagglutination by NDV specific MAb in two independent experiments (Table 2 and Table 3). For all NDV strains tested, haemagglutination was not inhibited by MAb directed against the F protein of NDV, or by the MAb against cIFNγ which served as a negative control. Likewise, haemagglutination was not inhibited by the MAb specific for HN protein of the Ulster strain. Surprisingly, the MAb 10B12 specific for the HN protein of the Hitchner strain inhibited haemagglutination induced by the F+HN strain. For the other NDV strains tested, haemagglutination was not inhibited by this MAb, as expected.

The HN specific MAb 8C11, 4D6, 6C6, 7B7 and 12B7 inhibited haemagglutination of the parent La Sota and the F mutant strain. The F mutant strain can thus not be discriminated from the parental NDV La Sota strain in this haemagglutination inhibition assay. Further, for the F+HN and HN+F mutant strains, all these HN specific MAb except the MAb 8C11 which was used for selection, inhibited haemagglutination. This indicates that in these double mutants, immunoselection with 8C11 resulted in the loss of the 8C11 epitope, while all other epitopes examined were conserved. Conversely, these HN specific MAb did virtually not (8C11, 4D6, 12B7 and 5A1) or only weakly (6C6, 7B7 and 7D4) inhibit the haemagglutination induced by the HN mutant (Table 3), indicating that for this mutant immunoselection with 8C11 had an effect on a number of epitopes spanning the entire HN molecule. Because the haemagglutination inhibition test only allows determining the expression of functionally active epitopes on the HN molecule, the expression of NDV specific epitopes by the HN and F molecules of the different NDV strains was assessed. For this, the binding of HN and F specific MAb with different purified NDV strains coated to ELISA plates was determined by indirect ELISA and quantified as absorbance. In general, the absorbances of the F+HN and the HN+F strains were lower than for the other strains, which most probably should be explained by a reduced amount of virus coated to the plate.

When this is taken in account, Table 4 shows that the reactivity of MAb remained unaltered where immunoselection was absent, i.e. in the HN and F proteins of respectively the F and HN mutant strains. Further, the F, F+HN and HN+F strains react identically with F specific MAb: in all these cases selection with the MAb 1C3 results thus in the loss of the epitopes seen by 1C3 and 10F2, while the epitopes seen by 2C1 and 12C4 appear to be conserved.

Two different types of selection were however observed for the selection of mutants with the HN specific MAb 8C11. At one side, the reactivities of the HN mutant strain and the parental La Sota strains with HN specific antibodies are identical, indicating that the HN, and also the F protein, remained largely unaltered and that in this case, immunoselection with the HN specific MAb 8C11 did not result in the disappearance of the epitope recognised by 8C11, or by any of the other MAb. Also, the reactivity of the HN+F mutant strain with HN specific antibodies remained unchanged by this selection. This was expected as the latter strain was derived from the HN strain.

At the other side, selection of the F mutant with 8C11 to produce the F+HN mutant resulted in the loss of the 8C11 epitope, while the other HN specific epitopes were conserved.

Combining Table 3 and Table 4 we can unambiguously characterize all mutated NDV strains. The HN mutant conserved all epitopes examined, but the lack of inhibition of haemagglutination by several MAb indicates possibly defective expression and functioning of the HN molecule. The F mutant is characterized by a mutation in the F protein only. The HN+F mutant also conserved all HN epitopes examined, but HI is only eliminated with the MAb 8C11 which was used for selection, indicating that the 8C11 epitope, although expressed is not functionally active anymore. Its F protein has the same antibody reactivity as the other strains selected with the F specific MAb 1C3, namely the F and the F+HN mutant strain. Typical for the F+HN strain, besides the mutant F protein, is that it has structurally and functionally lost the 8C11 epitope on the HN protein, whereas al other epitopes examined on this protein were conserved.

To further characterize all mutated NDV strains, the sequence of the genes encoding their HN and F proteins were sequenced as described by Meulemans et al. (2001). Table 5 shows the detected mutations, in comparison with the parental La Sota strain. The sequence of the HN and F proteins of the latter was related to the sequences of these proteins published in the EMBL database under accession number AF077761 (La Sota NDV, complete genome).

Example 3

Reduction of the Pathogenicity of NDV La Sota Mutant Strains for Embryos

Table 6 shows that the La Sota NDV strain widely used for post hatch vaccination is toxic to embryos and unsuitable, in current form, for in ovo use. Even very low doses of virus strongly depressed hatchability, while the few hatched chicks were of poor quality showing severe respiratory problems.

Table 7 demonstrates, although hatching percentages and neonatal survival tended to show high variability between groups, that the pathogenicity of both the HN and the F mutant for embryos and young chicks was reduced substantially in comparison with the parental La Sota strain. Indeed, Table 6 shows that inoculation of the latter strain resulted in 24 to 0% hatchability. Vaccination doses of 100 $EID_{50}$ or less tended to result in similar hatchability and neonatal survival in chicks treated with the HN mutant as in sham treated chicks.

In Table 8, Table 9 and Table 10 the influence of inoculation at ED18 with different doses of the NDV LaSota F+HN mutant strain and the HN+F mutant strain on the hatchability and neonatal survival are summarised. As for the F and HN mutant strains, hatching percentages and neonatal survival tended to show high variability between groups. However, it can be concluded that the pathogenicity of both the F+HN and the HN+F mutants was drastically reduced in comparison with the parental La Sota strain (Table 6). Moreover, hatchability and neonatal survival were generally higher for chicks inoculated with the double mutant strains than with the F and HN mutant strains.

Example 4

Administration of Mutant Viruses to SPF Embryos Induces a Virus Specific Immune Response In ovo administration of 100 $EID_{50}$ of the La Sota HN mutant to SPF embryos results in the production of NDV specific IgM and IgG antibodies that inhibit haemagglutination (FIG. 1). These antibody titres are of the same magnitude as the titres of age matched chicks receiving $10^5$ $EID_{50}$ La Sota at hatch by eye drop vaccination (FIG. 1).

Likewise, in ovo administration of $10^5$ (FIG. 2) and $10^2$ $EID_{50}$ (FIG. 3) of the La Sota F+HN mutant in SPF embryos results in the production of NDV specific IgM and IgG antibodies that inhibit haemagglutination. Serum antibody titres appear independent of the doses tested because similar kinetics and IgM titres are observed for both treatments. IgG titres seem even higher for $10^2$ $EID_{50}$ than for $10^5$ $EID_{50}$, but this should be interpreted cautiously because of the low number of chicks examined. (FIG. 2+3)

Example 5

Embryonic Administration of Mutant Viruses Induces a Virus Specific Protective Immune Response in the Presence of Maternal Antibodies In agreement with example 3, in ovo administration of the F+HN mutant to 18 day old embryos of commercial broilers did not result in a significant reduction of the hatchability (Table 11). Further, chicks receiving 0, $10^2$ and $10^3$ EID50 showed no or low post hatch mortality. In the isolator containing most birds, 6 of 46 chicks receiving $10^4$ EID50 died for unknown reasons. These mortalities occurred later than expected for possible virus induced mortality (days 8, 10, 11, 14, 18, 21 and 36) while no clinical symptoms, except feather picking were observed.

An NDV specific IgM response, which peaked around 14 days of age, is observed in chicks vaccinated at embryonic day 18 with $10^3$ and $10^4$ $EID_{50}$ of the F+HN mutant, but not in PBS treated chicks and in chicks receiving $10^2$ $EID_{50}$ of this mutant (FIG. 6). In the former chicks, NDV specific IgG, and HI titers, gradually increases with age, indicating isotype switching and an active production of NDV specific IgG (FIG. 5). In the latter groups, HI titers and NDV specific IgG of maternal origin gradually decrease to reach background levels around 3 weeks of age. Maternal NDV specific antibodies are thus not replaced by NDV specific antibodies produced by the chicks themselves.

HI titres (FIG. 4) and NDV specific IgM and IgG (not shown) were found in the serum of 14 and 21 day old SPF chicks (sentinels) housed in the same isolators as the chicks inoculated with $10^3$ and $10^4$ $EID_{50}$ of the F+HN strain, but not in the serum of 14 and 21 day old SPF chicks (sentinels)

housed in the same isolators as the control chicks and the chicks inoculated with $10^2$ EID$_{50}$ of the F+HN strain. This demonstrates that, if adequate doses are administered, the vaccine virus proliferates in the presence of maternal antibodies and is disseminated from vaccinated to non-vaccinated chicks The induction of NDV specific antibodies correlates well with protection against challenge with the very virulent TexasGB strain. Indeed, all chicks were protected against intramuscular challenge with $10^5$ EID$_{50}$ of the Texas GB strain in those groups (receiving $10^3$ or $10^4$ EID$_{50}$) where virus specific antibodies were detected in the serum (Table 12). On the contrary, if no antibodies were present (control chicks and chicks receiving $10^2$ EID$_{50}$ of F+HN), all chicks died or were moribund. An increase of NDV specific IgM, IgG and HI titres was observed in the chicks surviving challenge (FIG. 4, FIG. 5 and FIG. 6).

TABLE 3-continued

Characterisation of NDV La Sota strains by haemagglutination inhibition assay using NDV specific MAb

| Specificity | MAb | La Sota | F | HN | F + HN | HN + F |
|---|---|---|---|---|---|---|
| Ulster Italien (HN) | 3C5 | <2 | <2 | <2 | <2 | <2 |
| Hitchner (HN) | 10B12 | <2 | 2 | <2 | 5 | 2 |
| F protein | 1C3 | <2 | <2 | <2 | <2 | <2 |
|  | 2C1 | <2 | <2 | <2 | <2 | <2 |
|  | 10F2 | <2 | <2 | <2 | <2 | <2 |
|  | 12C4 | <2 | <2 | <2 | <2 | <2 |
| Anti cIFN γ |  | <2 | <2 | <2 | <2 | <2 |
| Positive control | PAb | 8 | 10 | 8 | 10 | 11 |

*Log$_2$ of the lowest dilution showing haemagglutination inhibition

TABLE 1

Neutralisation of antigenic variants after neutralisation using homologous MAb

| | | Virus titre after passage (TCID$_{50}$/ml) | | | |
|---|---|---|---|---|---|
| | Treatment | 1$^{st}$ passage* | 2$^{nd}$ passage | 3$^{rd}$ passage | 4$^{th}$ passage |
| F mutant | MAb 1C3 | 2.13 * 10$^4$ | >1.58 * 10$^9$ | 1.20 * 10$^9$ | 1.58 * 10$^8$ |
|  | No MAb | >1.58 * 10$^9$ | >1.58 * 10$^9$ | 2.39 * 10$^9$ | 2.13 * 10$^9$ |
| HN mutant | MAb 8C11 | 1.58 * 10$^6$ | 1.20 * 10$^6$ | 1.58 * 10$^7$ | 1.58 * 10$^6$ |
|  | No MAb | >1.58 * 10$^9$ | >1.58 * 10$^9$ | 2.39 * 10$^8$ | 5 * 10$^7$ |
| F + HN mutant | MAb 8C11 | 2.13 * 10$^5$ | 3.38 * 10$^5$ | 9.96 * 10$^8$ | |
|  | No MAb | 1.58 * 10$^9$ | 3.38 * 10$^8$ | 5 * 10$^8$ | |
| HN + F mutant | MAb 1C3 | 1.58 * 10$^2$ | 7.39 * 10$^7$ | 2.13 * 10$^7$ | |
|  | No MAb | 1.58 * 10$^8$ | 2.39 * 10$^8$ | 7.39 * 10$^7$ | |

*The virus titre of the parental NDV La Sota strain was 1.58 * 1010 EID50/ml).

TABLE 2

Characterisation of NDV La Sota strains by haemagglutination inhibition assay using NDV specific MAb

| Specificity | MAb | La Sota | F | HN | F + HN | HN + F |
|---|---|---|---|---|---|---|
| HN protein | 8C11 | 12* | 12 | 1 | 3 | 3 |
|  | 4D6 | 12 | 12 | 6 | 12 | 12 |
|  | 6C6 | 12 | 12 | 9 | 12 | 12 |
|  | 7B7 | 12 | 12 | 10 | 12 | 12 |
|  | 12B7 | 12 | 12 | 5 | 12 | 10 |
| IFN γ |  | 1 | 1 | 2 | 1 | 1 |

*Log$_2$ of the lowest dilution showing haemagglutination inhibition

TABLE 3

Characterisation of NDV La Sota strains by haemagglutination inhibition assay using NDV specific MAb

| Specificity | MAb | La Sota | F | HN | F + HN | HN + F |
|---|---|---|---|---|---|---|
| HN protein | 8C11 | 6* | 7 | <2 | <2 | <2 |
|  | 4D6 | 11 | >12 | <2 | >12 | 10 |
|  | 6C6 | 10 | 11 | 7 | >12 | 11 |
|  | 7B7 | 10 | >12 | 8 | >12 | 11 |
|  | 12B7 | 10 | 11 | <2 | 11 | 10 |
| La Sota (HN) | 7D4 | 10 | >12 | 7 | >12 | 10 |
| Lentogenous (HN) | 5A1 | 11 | 11 | 3 | >12 | 11 |

TABLE 4

Reactivities of HN specific MAb with different NDV strains in indirect ELISA

| Specificity | MAb | La Sota | F | HN | F + HN | HN + F |
|---|---|---|---|---|---|---|
| HN protein | 8C11 | 1.049* | 1.164 | 1.015 | 0.049 | 0.514 |
|  | 4D6 | 1.59 | 1.593 | 1.475 | 0.688 | 0.705 |
|  | 6C6 | 1.323 | 1.291 | 1.113 | 0.492 | 0.616 |
|  | 7B7 | 1.429 | 1.416 | 1.272 | 0.505 | 0.557 |
|  | 12B7 | 1.55 | 1.533 | 1.314 | 0.535 | 0.672 |
| La Sota (HN) | 7D4 | 1.52 | 1.475 | 1.415 | 0.536 | 0.676 |
| Lentogenous (HN) | 5A1 | 1.264 | 1.234 | 1.11 | 0.533 | 0.579 |
| Hitchner (HN) | 10B12 | 1.084 | 1.075 | 0.97 | 0.401 | 0.511 |
| F protein | 1C3 | 0.808 | 0.03 | 0.779 | 0.047 | 0.104 |
|  | 2C1 | 0.932 | 0.597 | 0.905 | 0.76 | 0.7 |
|  | 10F2 | 0.481 | 0.028 | 0.504 | 0.039 | 0.046 |
|  | 12C4 | 0.805 | 0.528 | 0.714 | 0.848 | 0.593 |
| Anti cIFN γ |  | 0.029 | 0.035 | 0.038 | 0.039 | 0.058 |
| Positive control | PAb | 2 | 1.931 | 1.993 | 1.803 | 1.737 |

*The binding of NDV specific antibodies is quantified as absorbance

TABLE 5

Sequence analysis of the genes coding for the F- and HN-glycoproteins of NDV La Sota strains

|  |  | La Sota | AF077761[b] | F | F + HN | HN | HN + F |
|---|---|---|---|---|---|---|---|
| F-gene | 72[a] | GAT (Asp) |  | TAT (Tyr) | TAT (Tyr) |  | GAA (Glu) |
|  | 101 | AGG (Arg) |  |  |  | ATG (Met) | ATG (Met) |
|  | 320 | CCA (Pro) | CCC (Pro) |  |  |  |  |
|  | 467 | CTC (Leu) | CTT (Leu) | CTT (Leu) | CTT (Leu) | CTT (Leu) | CTT (Leu) |
| HN-gene | 41 | ACA (Thr) |  |  |  | ACG (Thr) | ACG (Thr) |
|  | 115 | AAT (Asn) |  | AGT (Ser) | AGT (Ser) |  |  |
|  | 124 | AGG (Arg) |  | GGG (Gly) | GGG (Gly) |  |  |
|  | 158 | GAG (Glu) | GAA (Glu) |  |  |  |  |
|  | 160 | CTG (Leu) |  |  |  | CAG (Gln) |  |
|  | 193 | TTG (Leu) |  |  |  | TCG (Ser) | TCG (Ser) |
|  | 229 | CTG (Leu) |  |  | CGG (Arg) |  |  |
|  | 416 | CGG (Arg) | CGA (Arg) |  |  |  |  |
|  | 508 | AGC (Ser) | GGC (Gly) |  |  |  |  |

[a] Number of the codon, starting from the start codon
[b] As a reference, the sequences of the HN and F proteins of the La Sota strain used in our experiments was compared to the sequences of these proteins published in the EMBL database under accession number AF077761 (La Sota NDV, complete genome).

TABLE 6

Influence of inoculation at ED18 with different doses of the NDV La Sota strain on the hatchability of SPF eggs

| NDV strain | Dose ($EID_{50}$) | Total | Hatched |
|---|---|---|---|
| La Sota | 1000 | 17 | 0 (0%) |
|  | 100 | 17 | 2 (12%) |
|  | 10 | 17 | 0 (0%) |
|  | 1 | 17 | 4 (24%) |
| Control | 0 | 16 | 13 (81%) |

TABLE 7

Influence of inoculation at ED18 with different doses of the NDV La Sota HN mutant strain (Exp. 1–3) and the F mutant strain (Exp. 4) on the hatchability and neonatal survival

| Experiment | Dose ($EID_{50}$) | Eggs | Hatched | Neonatal survival (10 d) | Global survival (10 d) |
|---|---|---|---|---|---|
| 1 (HN mutant) | 100000 | 18 | 3 (17%) | N.D. |  |
|  | 10000 | 18 | 2 (11%) | N.D. |  |
|  | 1000 | 17 | 3 (18%) | N.D. |  |
|  | 100 | 17 | 8 (47%) | N.D. |  |
|  | 0 | 21 | 11 (52%) | N.D. |  |
| 2 (HN mutant) | 1000 | 21 | 16 (76%) | 10/16 (62%) | 48% |
|  | 100 | 21 | 5 (24%) | 3/5 (60%) | 14% |
|  | 10 | 21 | 15 (71%) | 13/15 (87%) | 62% |
|  | 1 | 20 | 11 (55%) | 10/11 (91%) | 50% |
|  | 0 | 21 | 13 (62%) | 10/13 (77%) | 47% |
| 3 (HN mutant) | 200 | 18 | 11 (61%) | 10/11 (91%) | 55% |
|  | 100 | 18 | 16 (89%) | 16/16 (100%) | 89% |
|  | 50 | 18 | 13 (72%) | 13/13 (100%) | 72% |
|  | 25 | 18 | 16 (89%) | 16/16 (100%) | 89% |
|  | 12.5 | 18 | 14 (78%) | 10/13 (77%) | 55% |
|  | 0 | 18 | 15 (83%) | 15/15 (100%) | 83% |
| 4 (F mutant) | 1000 | 15 | 10 (67%) | 3/10 (30%) | 20% |
|  | 100 | 15 | 7 (47%) | 3/7 (43%) | 20% |
|  | 10 | 15 | 11 (73%) | 4/11 (36%) | 27% |
|  | 1 | 15 | 8 (53%) | 4/8 (50%) | 27% |
|  | 0 | 15 | 12 (80%) | 10/12 (83%) | 67% |

TABLE 8

Influence of inoculation at ED18 with different doses of the NDV La Sota 1C3 + 8C11 mutant (F + HN) strain on the hatchability and neonatal survival

| Experiment | Dose ($EID_{50}$) | Eggs | Hatched | Neonatal survival (10 d) | Global survival (10 d) |
|---|---|---|---|---|---|
| Experiment 1 | $10^5$ | 20 | 18 (90%) | N.D.[a] | N.D. |
|  | $10^4$ | 20 | 14 (70%) | 13/14 (93%) | 13/20 (65%) |
|  | $10^3$ | 20 | 14 (70%) | 13/14 (93%) | 13/20 (65%) |
|  | $10^2$ | 20 | 17 (85%) | 13/17 (76%) | 13/20 (65%) |
|  | 10 | 20 | 17 (85%) | 13/17 (76%) | 13/20 (65%) |
|  | 0 | 20 | 11 (55%) | 9/11 (81%) | 9/20 (45%) |
| Experiment 2 | $10^6$ | 12 | 7 (58%) | 4/7 (57%) | 4/12 (33%) |
|  | $10^5$ | 12 | 11 (92%) | 7/11 (64%) | 7/12 (58%) |
|  | $10^4$ | 12 | 9 (75%) | 7/9 (78%) | 7/12 (58%) |
|  | $10^3$ | 12 | 12 (100%) | 10/12 (83%) | 10/12 (83%) |
|  | 0 | 14 | 12 (86%) | 11/12 (92%) | 11/12 (92%) |
| Experiment 3 | $10^4$ | 36 | 18[b] (50%) | 16/18 (90%) | 16/36 (44%) |
|  | $10^3$ | 36 | 27 (75%) | 24/27 (89%) | 24/36 (66%) |
|  | 0 | 36 | 31 (86%) | 30/31 (97%) | 30/36 (83%) |
| Experiment 4 | $10^4$ | 28 | 16[c] (73%) | 10/16 | 10/28 (36%) |
|  | $10^3$ | 28 | 22 (78%) | 18/22 | 18/28 (64%) |
|  | $10^2$ | 28 | 19[d] (68%) | 18/19 | 18/28 (64%) |
|  | 0 | 28 | 22 (78%) | N.D. | N.D. |

[a] 4 birds were sacrificed on D4 and D8 14/18 (78%)
[b] In 2 sacs, only 2 of 7 chicks hatched
[c] In one sac of dose $10^4$ and $10^2$, only 1 of chicks hatched
[d] In one sac of dose $10^2$, only 3 of 7 chicks hatched

TABLE 9

Influence of inoculation at ED18 with different doses of the NDV La Sota double mutant strains on the hatchability of NDV negative eggs

| Mutant virus strain | Dose ($EID_{50}$) | Total | Hatched | Neonatal survival (10 d) |
|---|---|---|---|---|
| (F+HN) | $10^6$ | 9 | 3 (33%)[a] | 1/3 (33%) |
|  | $10^5$ | 9 | 5 (56%) | 3/5 (60%) |
|  | $10^4$ | 9 | 7 (78%) | 5/7 (71%) |
|  | $10^3$ | 9 | 6 (67%) | 3/6 (50%) |

TABLE 9-continued

Influence of inoculation at ED18 with different doses of the NDV La Sota double mutant strains on the hatchability of NDV negative eggs

| Mutant virus strain | Dose ($EID_{50}$) | Total | Hatched | Neonatal survival (10 d) |
|---|---|---|---|---|
| (HN+F) | $10^6$ | 9 | 2 (22%) | 1/2 (50%) |
|  | $10^5$ | 9 | 2 (22%) | 1/2 (50%) |
|  | $10^4$ | 9 | 7 (78%) | 4/7 (57%) |
|  | $10^3$ | 9 | 3 (33%) | 3/9 (33%) |
| Control | 0 | 9 | 7 (78%) | 7/7 (100%) |

TABLE 10

Influence of inoculation at ED18 with different doses of the NDV La Sota HN + F strain on the hatchability of SPF eggs

| Dose ($EID_{50}$) | Total | Hatched | Neonatal survival (10 d) |
|---|---|---|---|
| $10^6$ | 12 | 5 (42%) | 1/5 (20%) |
| $10^5$ | 12 | 5 (42%) | 3/5 (60%) |
| $10^4$ | 12 | 4 (25%) | 2/4 (50%) |
| $10^3$ | 12 | 10 (83%) | 8/10 (80%) |
| 0 | 14 | 12 (86%) | 11/12 (92%) |
| $10^5$ | 19 | 11 (58%) | |
| $10^4$ | 19 | 12 (63%) | |
| $10^3$ | 19 | 17 (89%) | |
| $10^2$ | 19 | 12[a] (63%) | |
| 0 | 20 | 17 (85%) | |

[a] in one sac only 2 of 6 eggs hatched

TABLE 11

Influence of inoculation at ED18 with different doses of the NDV La Sota double mutant F+HN on the hatchability of eggs and post hatch mortality of commercial broiler chickens

| Mutant virus strain | Dose ($EID_{50}$) | Total | Hatched | Unexplained post hatch mortality |
|---|---|---|---|---|
| (F + HN) | $10^4$ | 51 | 46 (90%) | 6/46 |
|  | $10^3$ | 51 | 41 (80%) | 1 |
|  | $10^2$ | 51 | 41 (80%) | 0 |
| Control | 0 | 51 | 42 (82%) | 1 |

TABLE 12

In ovo vaccination with indicated doses of the F + HN mutant strain and effect on survival of commercial broiler chickens after intramuscular challenge with $10^5$ $EID_{50}$ of the Texas GB strain on day 43 post hatch.

| Treatment | n | Mortality by day 53 % |
|---|---|---|
| PBS treated | 11/12[a] | 92 |
| $10^2$ $EID_{50}$ F + HN | 12/12 | 100 |
| $10^3$ $EID_{50}$ F + HN | 0/12 | 0 |
| $10^4$ $EID_{50}$ F + HN | 0/9 | 0 |

[a] The surviving chick was moribund because of paralysis of its limbs

REFERENCES

Abenes G, Kida H, Yanagawa R. (1986) Antigenic mapping and functional analysis of the F protein of Newcastle disease virus using monoclonal antibodies. Arch Virol 90: 97-110

Ahmad J, Sharma J M (1992) Evaluation of a modified-live virus vaccine administered in ovo to protect chickens against Newcastle disease. Am J Vet Res: 53: 1999-2004.

Ahmad J, Sharma J M (1993) Protection against hemorrhagic enteritis and Newcastle disease in turkeys by embryo vaccination with monovalent and bivalent vaccines. Avian Dis 37:485-491

Chen L, Gorman J J, McKimm-Breschkin J, Lawrence L J, Tulloch P A, Smith B J, Colman P M, Lawrence M C (2001) The structure of the fusion glycoprotein of Newcastle disease virus suggests a novel paradigm for the molecular mechanism of membrane fusion. Structure 9: 255-266

Birrer M J, Udem S, Nathenson S, Bloom B R. (1981) Antigenic variants of measles virus. Nature 293: 67-69

EP 0848956 A1 (1998) In ovo vaccination against Newcastle disease

EP 1 074 614 A1 Mebatsion, (2001) A recombinant Newcastle disease virus for in ovo vaccination EP 0583998 Benejean J, Tuffereau M C, Coulon P, Flamand A, Lafay F (1994) Avirulent antirabies vaccine Fleming J O, Trousdale M D, el-Zaatari F A, Stohlman S A, Weiner L P (1986) Pathogenicity of antigenic variants of murine coronavirus JHM selected with monoclonal antibodies. J Virol 58: 869-75

Gerhard W, Webster R G. (1978) Antigenic drift in influenza A viruses. I. Selection and characterization of antigenic variants of A/PR/8/34 (HON1) influenza virus with monoclonal antibodies. J Exp Med 148: 383-92.

Haddad E E, Whiffill C E, Avakian A P, Ricks C A, Andrews P D, Thoma J A, Wakenell P S (1997). Efficacy of a novel infectious bursal disease virus immune complex vaccine in broiler chickens. Avian Dis 41: 882-889.

Long Le, Brasseur R, Wemers C, Meulemans G, Burny A (1988). Fusion (F) protein gene of Newcastle disease virus: sequence and hydrophobicity comparative analysis between virulent and avirulent strains. Virus Genes 1: 333-50.

Long Le, Portetelle D, Ghysdael J, Gonze M, Burny A, Meulemans G (1986) Monoclonal antibodies to hemagglutinin-neuramimidase and fusion glycoproteins of Newcastle disease virus: relationship between glycosylation and reactivity. J Virol 57: 1198-202.

Lubeck M D, Schulman J L, Palese P. (1980) Antigenic variants of influenza viruses: marked differences in the frequencies of variants selected with different monoclonal antibodies. Virology 102: 458-462

Meulemans G, Boschmans M, Decaestesstecker M, van den Bergh T P, Denis P, Cavanagh D (2001) Epidemiology of infectious bronchitis virus in Belgian broilers: a retrospective study, 1986 to 1995. Avian Path 30: 411-421

Meulemans G, Gonze M, Carlier M C, Petit P, Burny A, Le Long (1987b) Evaluation of the use of monoclonal antibodies to hemagglutinin and fusion glycoproteins of Newcastle disease virus for virus identification and strain differentiation purposes. Arch Virol 92: 55-62

Meulemans G, Gonze M, Carlier M C, Petit P, Burny A, Long Le (1987) Pathogenicity of antigenic variants of Newcastle disease virus Italian strain selected with monoclonal antibodies. Ann Rech Vet 18: 371-474

Meulemans G, Gonze M, Petit P, Long Le, Burny A (1986) Protective effects of HN & F glycoprotein-specific monoclonal antibodies on experimental Newcastle disease. Avian Path. 15: 761-768

Meulemans G, Roels S, van den Bergh T P, Godfroid G, De Caesteckere M (1998) Acute pancreatitis in chickens due to nonvirulent Newcastle disease virus. Vet Rec 143: 300-302

Neyt C, Geliebter J, Slaoui M, Morales D, Meulemans G, Burny A (1989) Mutations located on both F1 and F2 subunits of the Newcastle disease virus fusion protein confer resistance to neutralization with monoclonal antibodies. J Virol 63: 952-954

Reddy S K, Sharma J M, Ahmad J, Reddy D N, McMillen J K, Cook S M, Wild M A, Schwartz R D (1996). Protective efficacy of a recombinant herpesvirus of turkeys as an in ovo vaccine against Newcastle and Marek's diseases in specific-pathogen-free chickens. Vaccine 14: 469-477

Ricks C A, Avakian A, Bryan T, Gildersleeve R, Haddad E, Ilich R, King S, Murray L, Phelps P, Poston R, Whitfill C, Williams C. (1999) In ovo vaccination technology. Adv Vet Med 41: 495-515

Russell P H, Alexander D J (1983) Antigenic variation of Newcastle disease virus strains detected by monoclonal antibodies. Arch Virol 75: 243453

Sharma G, Greer W, Gildersleeve R P, Murray D L, Miles A M (1995). Field safety and efficacy of in ovo administration of HVT+SB-1 bivalent Marek's disease vaccine in commercial broilers. Avian Dis 39: 211-217

Sharma J M (1985). Embryo vaccination with infectious bursal disease virus alone or in combination with Marek's disease vaccine. Avian Diseases 29: 1155-1169

Sharma J M (1986). Embryo vaccination of specific-pathogen-free chickens with infectious bursal disease virus: tissue distribution of the vaccine virus and protection of hatched chickens against disease. Avian Dis 30: 776-780

Sharma J M (1987). Delayed replication of Marek's disease virus following in ovo inoculation during late stages of embryonal development. Avian Diseases 31(3):570-6.

Sharma J M (1999). Introduction to poultry vaccines and immunity. Adv Vet Med 41:481-94.

Sharma J M, Burmester B R. (1982). Resistance to Marek's disease at hatching in chickens vaccinated as embryos with the turkey herpesvirus. Avian Dis 26:134-149.

Sharma J M, Witter R L (1983). Embryo vaccination against Marek's disease with serotypes 1, 2 and 3 vaccines administered singly or in combination. Avian Dis 27: 453-463

Stone H, Mitchell B, Brugh M (1997). In ovo vaccination of chicken embryos with experimental Newcastle disease and avian influenza oil-emulsion vaccines. Avian Diseases 41: 856-863

Toyoda T, Gotoh B, Sakaguchi T, Kida H, Nagai Y (1988) Identification of amino acids relevant to three antigenic determinants on the fusion protein of Newcastle disease virus that are involved in fusion inhibition and neutralization. J Virol 62: 4427-4430

U.S. Pat. No. 4,040,388 Miller G E (1977) Method and apparatus for automatic egg injection U.S. Pat. No. 4,469,047 Miller G E (1984) Apparatus and method for injecting eggs U.S. Pat. No. 4,593,646 Miller G E, Sheeks P (1986) Egg injection method and apparatus U.S. Pat. No. 4,681,063 Hebrank J H (1987) High speed automated injection system for avian embryos U.S. Pat. No. 5,871,748 Thaxton J P, Tyczkowski J K, Thoma J A, Fredericksen T L, Whithfill C E (1999) Method of treating viral diseases in animals U.S. Pat. No. 5,427,791 (1995) Ahmad J, Sharma J, Embryonal vaccination of fowl against Newcastle disease is accomplished with ethyl methane sulfonate modified NDV-B1 virus U.S. Pat. No. 6,032,612 Williams D J (2000) Automated in ovo injection apparatus Wakenell P S, Sharma J M, (1986). Chicken embryonal vaccination with avian infectious bronchitis virus. Am J Vet Res 47: 933-938

Wakenell P S, Sharma J M, Slocombe R F (1995). Embryo vaccination of chickens with infectious bronchitis virus: histologic and ultrastructural lesion response and immunologic response to vaccination. Avian Dis 39: 752-765

Whitfill C E, Haddad E E, Ricks C A, Skeeles J K, Newberry L A, Beasley J N, Andrews P D, Thoma J A, Wakenell P S, (1995) Determination of optimum formulation of a novel infectious bursal disease virus (IBDV) vaccine constructed by mixing bursal disease antibody with IBDV. Avian Dis 39: 687-699

Whitfill C E, Ricks C A, Haddad E E, Andrews P A, Skeeles J K (1992) Infectious bursal disease (IBD) vaccine for day of age administration in broiler chickens. Poult Sci 71, Yusoff K, Nesbit M, McCartney H, Meulemans G, Alexander D J, Collins M S, Emmerson P T, Samson A C (1989) Location of neutralizing epitopes on the fusion protein of Newcastle disease virus strain Beaudette C. J Gen Virol 70: 3105-3109.

The invention claimed is:

1. An isolated attenuated mutant Newcastle disease La Sota virus suitable for in ovo vaccination of avian species comprising a mutation in the gene sequences encoding the HN and/or F glycoproteins of the virus, wherein the virus comprises a mutation selected from
    an Asp72Glu substitution in the F glycoprotein;
    a Leu160Gln, Leu193Ser or Leu229Arg substitution in the HN glycoprotein; and an Asp72Tyr substitution in the F glycoprotein and a Leu229Arg substitution in the HN glycoprotein.

2. An isolated attenuated mutant Newcastle disease La Sota virus strain chosen from the strains as deposited as La Sota mutant 1C3+8C11, under registration number CNCM I-2714, in the National Collection of Cultures of Microorganisms of the Pasteur institute in Paris.

3. A vaccine composition which provides protective immunity against Newcastle disease comprising an attenuated mutant Newcastle disease La Sota virus according to claim 1.

4. A method for the preparation of a vaccine for in ovo vaccination of avian species against Newcastle disease, comprising
    (a) providing an isolated attenuated mutant Newcastle disease La Sota virus according to claim 1, and
    (b) combining the attenuated mutant Newcastle disease La Sota virus with a pharmaceutically acceptable carrier or diluent,
thereby preparing a vaccine for in ovo vaccination of avian species against Newcastle disease.

5. A method for the preparation of a vaccine for post-hatch vaccination against Newcastle disease, comprising
    (a) providing an isolated attenuated mutant Newcastle disease La Sota virus according to claim 1, and
    (b) combining the attenuated mutant Newcastle disease La Sota virus with a pharmaceutically acceptable carrier or diluent, thereby preparing a vaccine for post-hatch vaccination against Newcastle disease.

6. A vaccine composition which provides protective immunity against Newcasde disease comprising an attenuated mutant Newcastle disease La Sota virus strain according to claim 2.

7. A method for the preparation of a vaccine for in ovo vaccination of avian species against Newcastle disease, comprising
   (a) providing an isolated attenuated mutant Newcastle disease La Sota virus strain according to claim 2, and
   (b) combining the attenuated mutant Newcastle disease La Sota virus strain with a pharmaceutically acceptable carrier or diluent, thereby preparing a vaccine for in ovo vaccination of avian species against Newcastle disease.

8. A method for the preparation of a vaccine for post-hatch vaccination against Newcastle disease, comprising
   (a) providing an isolated attenuated mutant Newcastle disease La Sota virus strain according to claim 2, and
   (b) combining the attenuated mutant Newcastle disease La Sota virus strain with a pharmaceutically acceptable carrier or diluent, thereby preparing a vaccine for post-hatch vaccination against Newcastle disease.

* * * * *